United States Patent
Bush

(10) Patent No.: US 7,834,187 B2
(45) Date of Patent: Nov. 16, 2010

(54) CRYSTALLINE VARIABLE HYDRATE OF (S)-6-(4-(2-((3-9H-CARBAZOL-4-YLOXY)-2-HYDROXYPROPYL)AMINO)-2-METHYLPROPYL)PHENOXY)-3-PYRIDINECARBOX AMIDE HEMISUCCINATE SALT

(75) Inventor: Julie Kay Bush, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 782 days.

(21) Appl. No.: 11/571,866

(22) PCT Filed: Jul. 14, 2005

(86) PCT No.: PCT/US2005/024886

§ 371 (c)(1),
(2), (4) Date: Jul. 25, 2007

(87) PCT Pub. No.: WO2006/019835

PCT Pub. Date: Feb. 23, 2006

(65) Prior Publication Data

US 2008/0058385 A1 Mar. 6, 2008

Related U.S. Application Data

(60) Provisional application No. 60/590,251, filed on Jul. 22, 2004.

(51) Int. Cl.
*C07D 401/12* (2006.01)
(52) U.S. Cl. .................................. 546/276.7
(58) Field of Classification Search .............. 546/276.7; 514/339
See application file for complete search history.

(56) References Cited

U.S. PATENT DOCUMENTS 6,627,646 B2 * 9/2003 Bakale et al. ............... 514/322
7,041,684 B2 * 5/2006 Rito et al. ................... 514/339

FOREIGN PATENT DOCUMENTS

EP 0 827 746 3/1998

OTHER PUBLICATIONS

Vippagunta et al., "Crystalline solids", Advanced Drug Delivery Reviews 48 (2001) 3-26.*
Ulicky et al., Comprehensive Dictionary of Physical Chemistry, NY Ellis Horwood PTR Prentice Hall, 1992, p. 21.*
Siilverman, The Organic Chemistry of Drug Design and Drug Action, NY: Academic Press, Inc. 1993, 72-76.*
Rowland and Tozer. "Clinical Pharmacokinetics, etc.," 1995, p. 123.*
Jain et al., "Polymorphism in Pharmacy", Indian Drugs, 1986, 23(6) 315-329.*
Chemical & Engineering News, Feb. 2003, 32-35.*
US Pharmacopia #23, Nationa Formulary #18, 1995, 1843-1844.*
Caira, "Crystalline Polymorphism, etc.," Topics in Current Chemistry, 198, Berline Heidelberg: Springer Vertag, 1998, pp. 164-208.*
Wilbraham et al. "Organic and biochemistry..." p. 250-251 (1985).*
Garattini "Active drug metabolites..." Clin. Pharmacokinetics v.10, p. 216-227 (1985).*
Muzaffar et al., "Polymorphism, etc.," Journal of Pharmacy (Lahore) 1979, 1(1), 59-66.*
Guillory (in Brittain ed.) "Polymorphism, etc.," NY: Marcel Dekker, Inc., 1999, 1-2, 125-146, 149-181, 183-226.*
CMU Pharmaceutical polymorphism, intenet p. 1-3 (2002) (printout Apr. 3, 2008).*
Singhal et al., "Drug polymorphism, etc.,"Advanced drug delivery reviews 56, 335-347 (2004)..*
Czeskis, B., et al., "Synthesis of β3 adrenergic receptor agonist LY377604 and its metabolite 4-hydroxycarbazole, labeled with carbon-14 and deuterium," *J Label Compd Radiopharm*, 48: 407-419 (2005).
Miller, JW, et al., "Stimulation of Energy Expenditure by LY377604, a beta3-Adrenergic Receptor Agonist with beta 1/2-Antagonist Properties in Healthy Male Subjects," *Obesity Research*, 7(Supp. 1), p. PF17. The North American Association for the Study of Obesity (1999).

* cited by examiner

*Primary Examiner*—Patricia L Morris
(74) *Attorney, Agent, or Firm*—John C. Demeter; Gilbert T. Voy

(57) ABSTRACT

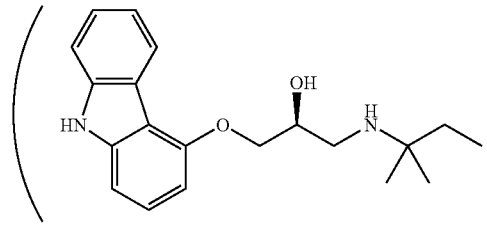

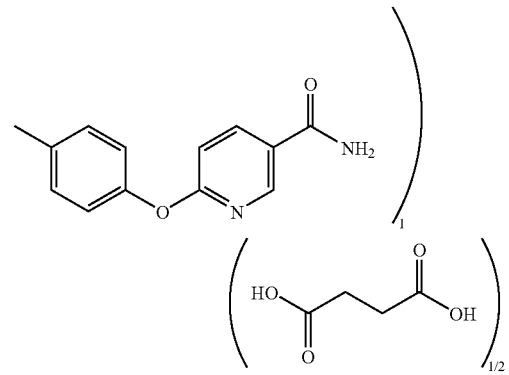

The present invention relates to a crystalline variable hydrate of (S)-(3-pyridinecarboxamide,6-[4-[2-[[3-(9H-carbazol-4-yloxy)-2-hydroxypropyl]amino]-2-methylpropyl]phenoxy])-hemi-succinate, a pharmaceutical formulation containing said salt and to methods for treating obesity and/or Type 2 diabetes using said salt.

5 Claims, 1 Drawing Sheet

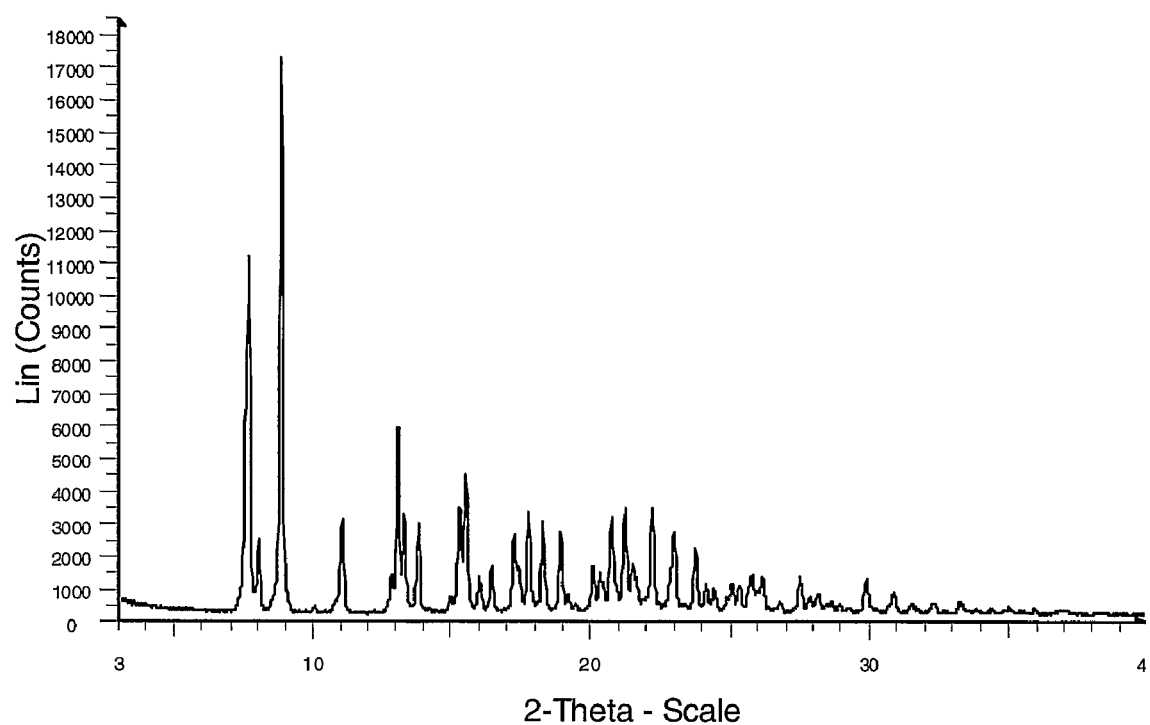

CRYSTALLINE VARIABLE HYDRATE OF (S)-6-(4-(2-((3-9H-CARBAZOL-4-YLOXY)-2-HYDROXYPROPYL)AMINO)-2-METHYLPROPYL)PHENOXY)-3-PYRIDINECARBOX AMIDE HEMISUCCINATE SALT

This application is a national phase application under 35 U.S.C. Section 371 for PCT/US2005/024886, filed Jul. 14, 2005, which claims the benefit under 35 U.S.C. Section 119 (e) of U.S. provisional patent application 60/590,251, filed Jul. 22, 2004.

BACKGROUND OF THE INVENTION

Compounds of formula II:

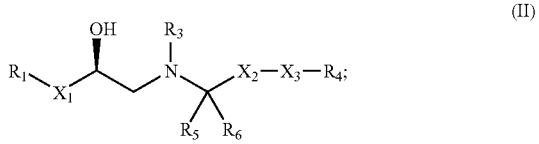

and pharmaceutically acceptable salts thereof, useful as selective $\beta_3$ receptor agonists, were disclosed by Heath, et al., in European Patent Publication No. 817,627 (Heath).

Example 126 from Heath disclosed the synthesis of a hemisuccinate salt of a formula II compound having the structure:

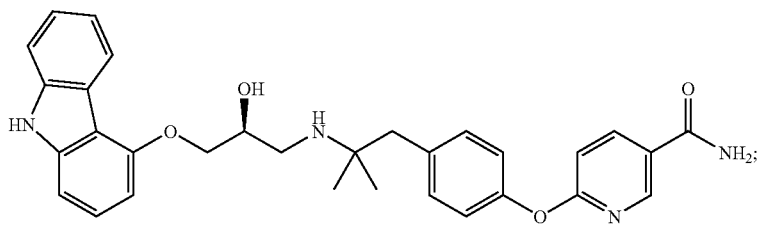

hereafter referred to as "SAM Classic".

Said synthetic procedures described the production of an "amorphous form" of SAM Classic "containing only trace residual ethanol". Heath described the production of the amorphous SAM Classic by solvent exchange of the ethanol in the crystalline ethanolic solvate of SAM Classic with water. In particular, Heath taught that "The mixture (from the water slurry) was vacuum filtered, and the filter cake was washed with water (3×100 ml). The solid was air dried under vacuum for approximately 2 hours then in a vacuum oven (65° C.) overnight. This gave (amorphous) product as an off white solid." Thus, Heath discloses that in the process of drying the wet cake material, the crystal structure of the initially isolated material (present as a wet cake) collapsed to form the amorphous SAM Classic.

Poorly crystalline materials, in particular amorphous materials, are typically less desirable than highly crystalline materials for formulation processing. In addition, it is generally not desirable to formulate pharmaceuticals containing substantial amounts of organic solvent due to potential solvent toxicity to the recipient thereof and changes in potency of the pharmaceutical as a function of the solvent. Although the amorphous SAM Classic prepared by the procedures taught in '474 could be used as a pharmaceutical, it would be highly desired and advantageous to find a stable crystalline form of SAM Classic that did not contain substantial amounts of organic solvent within its crystal structure which could be reproducibly and efficiently prepared on a commercial scale.

Surprisingly, and in accordance with the invention, it has now been discovered that a crystalline hydrate of SAM Classic is capable of reproducible production, isolation and formulation on a commercial scale, is sufficiently stable for use in oral formulations, and can be produced and isolated in a highly crystalline state.

BRIEF SUMMARY OF THE INVENTION

The present invention relates to a crystalline variable hydrate of (S)-(3-pyridinecarboxamide,6-[4-[2-[[3-(9H-carbazol-4-yloxy)-2-hydroxypropyl]amino]-2-methylpropyl] phenoxy])-hemi-succinate salt wherein the water content of said hydrate by weight is between 6 and 11% when measured at 22±5° C. and between 10-80% relative humidity. This crystalline material is hereafter referred to "SAM Classic Hydrate".

The present invention further relates to SAM Classic Hydrate having an X-ray diffraction pattern which comprises the following peaks: 7.6±0.1 and 8.8±0.1° in 2θ; when the pattern is obtained at 20-25° C. and 25-30% relative humidity (RH) using a copper radiation source (CuKα; λ=1.54056 Å).

In another embodiment, the present invention relates to a pharmaceutical composition containing SAM Classic Hydrate and a pharmaceutical carrier. In still another embodiment, the pharmaceutical compositions of the present invention may be adapted for use in treating obesity and/or Type II diabetes.

Moreover, the present invention relates to methods for treating obesity and/or Type II diabetes which comprise administering to a patient in need thereof an effective amount of SAM Classic Hydrate.

In addition, the present invention is related to SAM Classic Hydrate for treating obesity and/or Type II diabetes. In yet another embodiment, the present invention relates to the use of SAM Classic Hydrate for the manufacture of a medicament for the treatment of obesity and/or Type II diabetes.

BRIEF DESCRIPTION OF THE FIGURES

FIG. 1 is a representative XRD pattern for SAM Classic Hydrate.

DETAILED DESCRIPTION OF THE INVENTION

For the purposes of the present invention, as claimed herein, the following terms are defined below.

The term "pharmaceutical" when used herein as an adjective means substantially non-deleterious.

The term "patient" as used herein refers to humans and non-human animals such as companion animals (dogs, cats, horses and the like). A preferred patient is a human.

The terms "treating" and "treat" as used herein means alleviating, ameliorating, preventing, prohibiting, restraining, slowing, stopping, or reversing the progression or severity of a pathological condition, or sequela thereof, described herein.

The term "a patient in need thereof" is a patient suffering from the claimed pathological condition or sequela thereof as determined by medical diagnosis, i.e., as determined by the attending physician.

As used herein, the term "effective amount" means an amount of SAM Classic Hydrate that is capable of treating the conditions described herein.

According to Heath, removal of the water from the wet cake precursor to the amorphous SAM Classic described therein via air drying under vacuum for approximately 2 hours then in a vacuum oven at 65° C. overnight caused the crystal structure of this precursor to collapse. Thus, Heath suggests that the crystal structure of SAM Classic Hydrate is not stable when prepared using the standard laboratory/manufacturing techniques described therein and, therefore, not suitable for development as the active pharmaceutical ingredient (API). As described herein, Applicants have found commercially relevant methods for the preparation and isolation of SAM Classic Hydrate.

Characterization of Sam Classic Hydrate

Various methods, including moisture sorption analysis, Karl Fischer analysis, X-ray powder diffraction (XRD) and $^{13}C$ solid-state nuclear magnetic resonance (SSNMR), are used to characterize SAM Classic Hydrate.

The moisture sorption profile for SAM Classic Hydrate reveals that it is a non-stoichiometric hydrate. The SAM Classic Hydrate crystal structure retains approximately 6-11% water between 10 and 80% relative humidity. The hydrate rapidly equilibrates with the atmosphere, such that the water content observed by analytical techniques is a function of the relative humidity at which the sample was equilabrated.

The water content of SAM Classic Hydrate may be determined by volumetric Karl Fischer titration employing a suitable Karl Fischer (KF) titration system, e.g., a Metrohm® system. Water content, via KF, is determined via the quantitative reaction of water with iodine and sulfur dioxide while in the presence of alcohol and an organic base such as pyridine. The amount of water is quantitated by end-point determination using an appropriately calibrated titrant. Method Conditions: Standard—Purified water; Titer—Hydranal Composite 2K Pyridine-Free reagent, or AquaStar Comp2 Pyridine-Free reagent or equivalent (2 mg/mL); Volumetric Flow Rate—5 ml/min; Agitator Speed—the maximum speed at which air bubbles are not being created in the titration vessel. Procedure: Transfer an aliquot of sample (200 mg or more) to the titration vessel. Completely dissolve the sample in anhydrous methanol prior to analysis. Perform first titration. Perform a second titration using approximately the same amount of SAM Classic Hydrate employed in the first run. Calculate the average of the two results.

Calculations:

% Water=$[([T] \times V_{titer})/Wt_{sample}] \times 100\%$

[T]=Titer concentration $V_{titer}$=Volume of titer used in the titration $Wt_{Sample}$=Weight of sample in mg The X-ray powder diffraction patterns are obtained on a Siemens D5000 X-ray powder diffractometer which is equipped with a CuKα source (λ=1.54056 Å) operated at 50 kV and 40 mA with a Kevex solid state Si(Li) detector. The samples are scanned from 4 to 40° in 2θ at 3.0 seconds per step size of 0.02° with 1 mm divergence and receiving slits and a 0.1 mm detector slit. The dry powder is dusted onto a low background sample holder for analysis at 20-25° C. and 25-30% relative humidity (RH).

A representative XRD trace of SAM Classic Hydrate is shown in FIG. 1. The XRD pattern features sharp peaks and a flat baseline, indicative of highly crystalline material. The angular peak positions in 2θ and corresponding $I/I_O$ data for all peaks with intensities equal to or greater than 10% of the largest peak are tabulated in Table 1. All data in Table 1 is expressed with an accuracy of ±0.1° in 2θ.

TABLE 1

| Angle 2θ | $I/I_o$ (%) |
| --- | --- |
| 7.5 | 34.9 |
| 7.6 | 64.7 |
| 8.0 | 14.4 |
| 8.8 | 100.0 |
| 11.0 | 18.1 |
| 13.1 | 34.3 |
| 13.3 | 18.9 |
| 13.8 | 17.1 |
| 15.3 | 19.9 |
| 15.5 | 25.9 |
| 17.3 | 15.1 |
| 17.8 | 19.2 |
| 18.3 | 17.3 |
| 18.9 | 15.7 |
| 20.7 | 18.3 |
| 21.2 | 19.9 |
| 21.5 | 10.1 |
| 22.2 | 20.0 |
| 23.0 | 15.7 |
| 23.8 | 12.8 |

It is well known in the crystallography art that, for any given crystal form, the relative intensities of the diffraction peaks may vary due to preferred orientation resulting from factors such as crystal morphology. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that, for any given crystal form, the angular peak positions may vary slightly. For example, peak positions can shift due to a variation in the temperature or humidity at which a sample is analyzed or sample displacement. In the present case, a peak position variability of ±0.1° in 2θ will take into account these potential variations without hindering the unequivocal identification of SAM Classic Hydrate.

Based on peak intensities as well as peak positions, SAM Classic Hydrate may be identified by the presence of peaks at 7.6±0.1 and 8.8±0.1° in 2θ; when the pattern is obtained at 20-25° C. and 25-30% relative humidity (RH) using a copper radiation source (CuKα; λ=1.54056 Å). The presence of the SAM Classic Hydrate may be further verified by peaks at 13.1±0.1 and 15.5±0.1° in 2θ; when the pattern is obtained as described above and even further verified by the presence of peaks at 8.0±0.1, 11.0±0.1, 13.3±0.1, 13.8±0.1, and 15.3±0.1° in 2θ; when the pattern is obtained as described above.

$^{13}C$ SSNMR analysis is performed with a Varian Unity Inova 400 MHz spectrometer operating at a carbon frequency of 100.578 MHz, using high-power proton decoupling, cross polarization (CP) and magic angle spinning (MAS) at 7.0 kHz. Acquisition parameters are as follows: 90° proton r.f. pulse width 4.0 μs, contact time 1.5 ms, pulse repetition time 5 s, spectral width 50 kHz, and acquisition time 50 ms. Chemical shifts, expressed as parts per million, are referenced to the methyl group of hexamethylbenzene (δ=17.3 ppm) by sample replacement. The magic angle is adjusted by optimizing the sidebands of the $^{79}$Br signal of KBr as described by Frye and Maciel (Frye J. S. and Maciel G. E., *J. Magn. Reson.*, 1982, 48, 125).

SAM Classic Hydrate may be identified by the presence of isotropic peaks at: 59.8±0.1, 111.4±0.1 and 151.4±0.1 ppm when the sample has been equilibrated at 33% R. H. prior to data collection. SAM Classic Hydrate is further characterized by solid-state $^{13}$C NMR resonances at 99.2±0.1, 102.4±0.1, 134.9±0.1, 146.9±0.1 and 149.2±0.1 ppm when the sample has been equilibrated at 33% R.H. prior to data collection.

The amount (weight percentage) of solvent, such as methanol, ethanol or ethyl acetate, present in the crystalline material may be determined by headspace gas chromatography with flame ionization detection. A sample of the crystalline solid (50 mg) is weighed in a headspace vial and dissolved in 2 mL of dimethylsulfoxide. The vial is incubated at 80° C. for 5 minutes and then analyzed using a DB624 column (30 meter, 0.53 mm i.d., 3 micron film thickness). The column temperature is held at 40° C. for 10 minutes to elute the solvents of interest, then the oven temperature is increased to 240° C. to elute the sample solvent peak. The GC utilizes helium as a carrier gas at a flow of approximately 5 ml/minute. The inlet temperature is set to 220° C. with a split ratio of 1:5 and injection volume of 1 mL. The detector temperature is 250° C. The amount of solvent is determined by comparison to solvent standards prepared at known concentrations. A linear least squares calibration curve is constructed using standard concentrations (in mg/mL) and standard peak areas. The solvent peak areas in the sample injections are compared to the calibration curve to determine the concentration of solvent in each of the sample injections. The percentage of solvent is calculated using the following formula:

$$\% \text{ solvent} = \frac{(\text{amount solvent found in mg/mL})(2.0 \text{ mL})}{\text{mg sample}} \times 100$$

The amount (weight percentage) of chemical impurities present in the crystalline material may be determined using reversed-phase HPLC with UV detection. A sample of the crystalline solid (approximately 10 mg) is weighed into a 25-ml volumetric flask and diluted with 70/30 (v/v) mixture of methanol/water. An aliquot of this solution is assayed using a Zorbax SB-Phenyl column (25 cm×4.6 mm I.D., 5 micron particles). The injection volume is 5 microliters with an autosampler temperature of 5° C. The detector wavelength is 240 nm and the column flow rate is 1.0 ml/minute. The following gradient solvent system is used:

| Time (minute) | % A | % B |
|---|---|---|
| 0 | 100 | 0 |
| 32 | 0 | 100 |
| 33 | 0 | 100 |
| 34 | 100 | 0 |
| 44 | 100 | 0 |

A: 50% Methanol:50% Water:0.1% Trifluoroacetic Acid
B: 75% Methanol:25% Water:0.1% Trifluoroacetic Acid The area percentage of the impurities is calculated using the following formula $$\% \text{ Total Impurities} = \frac{\text{Sum of the impurity peak areas}}{\text{Total of all peak areas}} \times 100$$

Synthesis

The crystalline ethanol solvate of SAM Classic (719.35 g) is combined with 5.4 L of deionized water. The resulting slurry is stirred at ambient temperature for approximately 25 hours. The slurry is filtered using nitrogen pressure. The filter cake is rinsed with 2.165 L of water. The filter cake is dried at ambient temperature under a purge of nitrogen that had been bubbled through a saturated solution of potassium acetate in water to maintain a constant humidity. The nitrogen going into the filter has a relative humidity of 22.9% and is at 15 PSI of pressure. The filter cake is dried until the % water is 8.5 to 11% as measured by KF analysis as described herein. After approximately 112 hours, the KF is 8.85% and 666.20 g of SAM Classic Hydrate is obtained.

Formulation

The SAM Classic Hydrate of the present invention is preferably formulated in a unit dosage form prior to administration to the recipient patient. SAM Classic Hydrate is preferably formulated employing a dry blend process. Although SAM Classic Hydrate on its own has very poor flow that could have lead to flowability (cohesiveness of the powder) problems during filling (leading to poor control on weight uniformity) and/or homogeneity problems after mixing, the formulations described herein have acceptable mixing and uniformity attributes, even with the high strength.

FORMULATION EXAMPLES

| Ingredient | Quantity (mg/capsule) |
|---|---|
| SAM Classic Hydrate | 16.7 (15.0 free base) |
| Partially pregelatinized starch RLC | 388.3 |
| Starch flowable powder with 5% silicon | 45.0 |

| Ingredient | Quantity (mg/capsule) |
|---|---|
| SAM Classic Hydrate | 55.6 (50.0 mg free base) |
| Partially pregelatinized starch RLC | 349.4 |
| Starch flowable powder with 5% silicon | 45.0 |

| Ingredient | Quantity (mg/capsule) |
| --- | --- |
| SAM Classic Hydrate | 111.3 (100 mg of free base) |
| Partially pregelatinized starch RLC | 316.2 |
| Starch flowable powder with 5% silicon | 47.5 |

Sieve partially pregelitinized starch through a 10 mesh screen. Add the pregelatinized starch to a tumble bin. Add SAM Classic Hydrate (API) to tumble bin by layering API in between the starch. Mix for 15 minutes at 13 rpm. Pass the resultant mixture through a Comill (screen size: ~610 μm). Transfer mixture back to tumble bin and mix for 30 minutes at 13 rpm. Sieve the starch flowable powder (5% silicon) through a 10 mesh screen and add to mixture in tumble bin. Mix for 15 minutes at 13 rpm. Fill into size 0 capsules. Refrigerate filled capsules in sealed foil bags at 2-8° C.

Demonstration of Function

SAM Classic free base was disclosed in WO 98/09625 (Example 87 therein), the contents of which are herein incorporated by reference. In the "Functional.Agonist B3 assay", this free base material was described as having at least 30% ... of isoproterenol's response at a single dose of 50 mmol. Dose response titrations on the agonists described reveal $EC_{50}$ values <10 mM ...

When screened against the $B_1$ and $B_2$ receptors in the functional assay, dose titration experiments indicate that greatly reduced or no receptor stimulation is observed with the compounds of the invention.

Utilities

The diseases, disorders or conditions for which SAM Classic Hydrate is useful in treating include, but are not limited to, Type 2 diabetes mellitus and obesity. Human patients in need of obesity and/or Type 2 diabetes treatment are typically those with a body mass index (BMI)>30 or those with a BMI≧27 when co-morbidities, e.g., hypertension, high cholesterol, heart disease or diabetes are present.

Dose

The specific dose administered is determined by the particular circumstances surrounding each situation. These circumstances include: the route of administration (preferably oral), the prior medical history of the recipient, the pathological condition or symptom being treated, the severity of the condition/symptom being treated, and the age of the recipient. The recipient patient's physician should determine the therapeutic dose administered in light of the relevant circumstances. Generally, an effective minimum daily dose will be about 1 mg or more. Typically, an effective maximum daily dose will not exceed about 600 mg.

Combination Therapy

SAM Classic free base, or a pharmaceutical salt thereof (preferably the hemi-succinate salt of SAM Classic free base, more preferably SAM Classic Hydrate), may be used in combination with other drugs that are used in the treatment of the diseases or conditions for which the present salts are useful, e.g., treatment of obesity and/or type 2 diabetes. Such other drug(s) may be administered, by a route and in an amount commonly used therefore, contemporaneously or sequentially with the free base of SAM Classic (or salt thereof). When SAM Classic free base, or a salt thereof, is used contemporaneously with one or more other drugs, a pharmaceutical unit dosage form containing such other drugs in addition to SAM Classic free base (or salt thereof) may be preferred.

Accordingly, the pharmaceutical compositions of the present invention include those that also contain one or more other active ingredients, in addition to SAM Classic free base (or salt thereof).

A preferred combination therapy for the treatment of obesity is the use of SAM Classic Hydrate in combination with Meridia® (sibutramine or active metabolites of sibutramine, e.g., desmethyl sibutramine and di-desmethyl sibutramine, preferably with sibutramine hydrochloride mono-hydrate) or with Xenical® (orlistat).

I claim:

1. A crystalline variable hydrate of (S)-(3-pyridinecarboxamide, 6-[4-[2-[[3-(9H-carbazol-4-yloxy)-2-hydroxypropyl]amino]-2-methylpropyl]phenoxy])-hemi-succinate salt wherein the water content of said hydrate by weight is between 6 and 11% when measured at 22±5° C. and between 10-80% relative humidity; ethanol is present at ≦1% weight; and having an X-ray diffraction pattern which comprises the following peaks: 7.6±0.1, 8.0±0.1, 8.8±0.1, 11.0±0.1, 13.1±0.1, 13.3±0.1, 13.8±0.1, 15.3±0.1 and 15.5±0.1° in 2θ; when the pattern is obtained at 20-25° C. and 25-30% relative humidity (RH) using a copper radiation source (CuKα; λ=1.54056 Å).

2. The hydrate of claim 1 wherein the water content is between 7.5 and 11%.

3. The hydrate of claim 1 having a solid-state $^{13}$C nuclear magnetic resonance spectrum which comprises peaks at the following chemical shifts: 59.8±0.1, 111.4±0.1 and 151.4±0.1 ppm when the hydrate has been equilibrated at 33% R.H. prior to data collection.

4. The hydrate of claim 3 having a solid-state $^{13}$C nuclear magnetic resonance spectrum which further comprises peaks at the following chemical shifts: 99.2±0.1, 102.4±0.1, 134.9±0.1, 146.9±0.1 and 149.2±0.1 ppm.

5. The hydrate of claim 1 wherein the amount of chemical impurities present by weight is <2%.

* * * * *

UNITED STATES PATENT AND TRADEMARK OFFICE
CERTIFICATE OF CORRECTION

PATENT NO. : 7,834,187 B2
APPLICATION NO. : 11/571866
DATED : November 16, 2010
INVENTOR(S) : Julie Kay Bush It is certified that error appears in the above-identified patent and that said Letters Patent is hereby corrected as shown below:

First Page, Item [56] Column 1, Line 5 (Other Publications): Delete "Siilverman," and insert -- Silverman, -- therefor.

First Page, Item [56] Column 1, Line 7 (Other Publications): Delete "Rowland and Tozer." and insert -- Rowland and Tozer, -- therefor.

First Page, Item [56] Column 1, Line 11 (Other Publications): Delete "Pharmacopia" and insert -- Pharmacopeia -- therefor.

First Page, Item [56] Column 1, Line 11 (Other Publications): Delete "Nationa" and insert -- National -- therefor.

First Page, Item [56] Column 2, Line 2 (Other Publications): Delete "Berline" and insert -- Berlin -- therefor.

First Page, Item [56] Column 2, Line 2 (Other Publications): Delete "Vertag" and insert -- Verlag -- therefor.

First Page, Item [56] Column 2, Line 10 (Other Publications): Delete "intenet" and insert -- internet -- therefor.

Signed and Sealed this
Eighth Day of February, 2011

David J. Kappos
*Director of the United States Patent and Trademark Office*